US009878041B2

(12) United States Patent
Lee et al.

(10) Patent No.: US 9,878,041 B2
(45) Date of Patent: *Jan. 30, 2018

(54) CYANOACRYLATE TISSUE ADHESIVES

(71) Applicant: Adhezion Biomedical, LLC, Wyomissing, PA (US)

(72) Inventors: Jeoung Soo Lee, Clemson, SC (US); Charles Kenneth Webb, Clemson, SC (US); Robert Zimmerman, White Plains, NY (US); Rafael Ruiz, Sr., Hudson, NC (US); Sheng Zhang, Hickory, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 556 days.

This patent is subject to a terminal disclaimer.

(21) Appl. No.: 14/075,257

(22) Filed: Nov. 8, 2013

(65) Prior Publication Data
US 2014/0066364 A1   Mar. 6, 2014

Related U.S. Application Data

(63) Continuation of application No. 12/742,868, filed as application No. PCT/US2007/084607 on Nov. 14, 2007, now Pat. No. 8,613,952.

(51) Int. Cl.
| | |
|---|---|
| A61K 9/14 | (2006.01) |
| A61K 47/32 | (2006.01) |
| A61L 24/00 | (2006.01) |
| A61L 24/04 | (2006.01) |
| A61K 31/513 | (2006.01) |
| A61K 38/12 | (2006.01) |
| A61B 17/00 | (2006.01) |

(52) U.S. Cl.
CPC ............ *A61K 47/32* (2013.01); *A61K 31/513* (2013.01); *A61K 38/12* (2013.01); *A61L 24/0015* (2013.01); *A61L 24/0042* (2013.01); *A61L 24/043* (2013.01); *A61B 17/00491* (2013.01); *A61L 2300/406* (2013.01); *A61L 2300/408* (2013.01); *A61L 2300/41* (2013.01); *A61L 2300/416* (2013.01)

(58) Field of Classification Search
None
See application file for complete search history.

(56) References Cited

U.S. PATENT DOCUMENTS

| | | |
|---|---|---|
| 211,104 A | 1/1879 | Mulford |
| 334,046 A | 1/1886 | Pinkham |
| 1,221,227 A | 4/1917 | Schulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |

(Continued)

FOREIGN PATENT DOCUMENTS

| | | |
|---|---|---|
| DE | 2010 3336 | 5/2001 |
| EP | 0127466 | 12/1984 |

(Continued)

OTHER PUBLICATIONS

"Aclar®/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing&mod=Publications%3A%3AArticle&mid=8F3A7027421841978F18BE895F87F791&tier=4&id=6EC6964EB29D46D8A297E499E57A4164.

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "The Degradation of Cyanoacrylate Tissue Adhesive, pt. 1", Surgery, vol. 58, Iss. 2, Aug. 1965, pp. 424-430.

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

(Continued)

*Primary Examiner* — Dennis J Parad
(74) *Attorney, Agent, or Firm* — Stradley Ronon Stevens & Young, LLP

(57) ABSTRACT

A tissue adhesive including cyanoacrylate and polyethylene glycol (PEG), wherein the PEG remains a polyether and wherein the tissue adhesive is bioabsorbable. A tissue adhesive including cyanoacrylate bulk monomer and cyanoacrylate nanoparticles containing a therapeutic therein. A kit for applying tissue adhesive, including the tissue adhesive described above and an applicator. Methods of accelerating degradation of a cyanoacrylate tissue adhesive applying a tissue adhesive, closing an internal wound, administering a therapeutic to tissue, treating cancer, and preventing infection in a wound. Methods of method of making a bioabsorbable tissue adhesive and making a therapeutic tissue adhesive.

9 Claims, 15 Drawing Sheets

(56) References Cited

U.S. PATENT DOCUMENTS

| | | |
|---|---|---|
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,583,114 A * | 12/1996 | Barrows ............... A61L 24/043 424/179.1 |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,803,086 A | 9/1998 | Scholz et al. |
| 5,807,563 A | 9/1998 | Askill et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,323,275 B2 | 11/2001 | Takahashi et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B2 | 9/2004 | Kotzey |
| 6,802,416 B1 | 10/2004 | D'Alessio et al. |
| 6,849,082 B2 | 2/2005 | Azevedo |
| 6,881,421 B1 | 4/2005 | daSilveira |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |

(56) References Cited

U.S. PATENT DOCUMENTS

| | | | |
|---|---|---|---|
| 6,977,278 | B1 | 12/2005 | Misiak |
| 6,995,227 | B2 | 2/2006 | Ryan et al. |
| 7,255,874 | B1 | 8/2007 | Bobo et al. |
| 8,613,952 | B2* | 12/2013 | Lee ........................ A61K 47/32 424/443 |
| 2003/0044380 | A1* | 3/2003 | Zhu ....................... A61B 17/085 424/78.37 |

FOREIGN PATENT DOCUMENTS

| | | |
|---|---|---|
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO1996/014292 | 5/1996 |
| WO | WO1996/23532 | 8/1996 |
| WO | WO1999/10020 | 3/1999 |
| WO | WO2003/070257 | 8/2003 |
| WO | WO2004/045498 | 6/2004 |
| WO | WO2006/073922 | 7/2006 |
| WO | WO2009/003017 | 12/2008 |

OTHER PUBLICATIONS

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Fussnegger, B. "Poloxamers (1) Lutrol® F 68 (Poloxamer 188)." BASF ExAct, No. 3, Nov. 1999, 5-6.

Garnier-Suillerot et al., "Analysis of Drug Transport Kinetics in Multidrug-resistant Cells: Implications for Drug Action" Current Medicinal Chemistry, 2001, 8, 51-64.

Hansen, "Fast Cure—High moisture vapor transmission rate adhesives improve wound care." Adhesives Age Mar. 2003, pp. 22, 24 and 25.

Huang, et al., "Core-shell type of nanoparticles composed of poly[(n-butyl cyanoacrylate)-co-(2-octyl cyanoacrylate)] copolymers for drug delivery application: Synthesis, characterization and in vitro degradation", Intl. J. of Pharm., 325 (2006) 132-139.

International Search Report and Written Opinion dated Apr. 3, 2008 for international application No. PCT/US2007/084607.

Lehman et al., "Toxicity of Alkyl 2-Cyanoacrylates", Archives of Surgery, vol. 93, Issue 3, Sep. 1966, pp. 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

O'Sullivan, et al., "Hydrolysis of poly (n-butylcyanoacrylate) nanoparticles using esterase", Polymer Degradation and Stability, 78 (2002) 7-15.

Quinn, J.V., "Clinical Approaches to the Use of Cyanoacrylate Tissue Adhesives", Tissue Adhesives in Clinical Medicine, Second Edition, 2005, BC Decker, Inc., pp. 27-76.

Sullivan, et al., "In vitro degradation of insulin-loaded poly (n-butylcyanoacrylate) nanoparticles", Biomaterials, 25 (2004) 4375-4382.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

\* cited by examiner

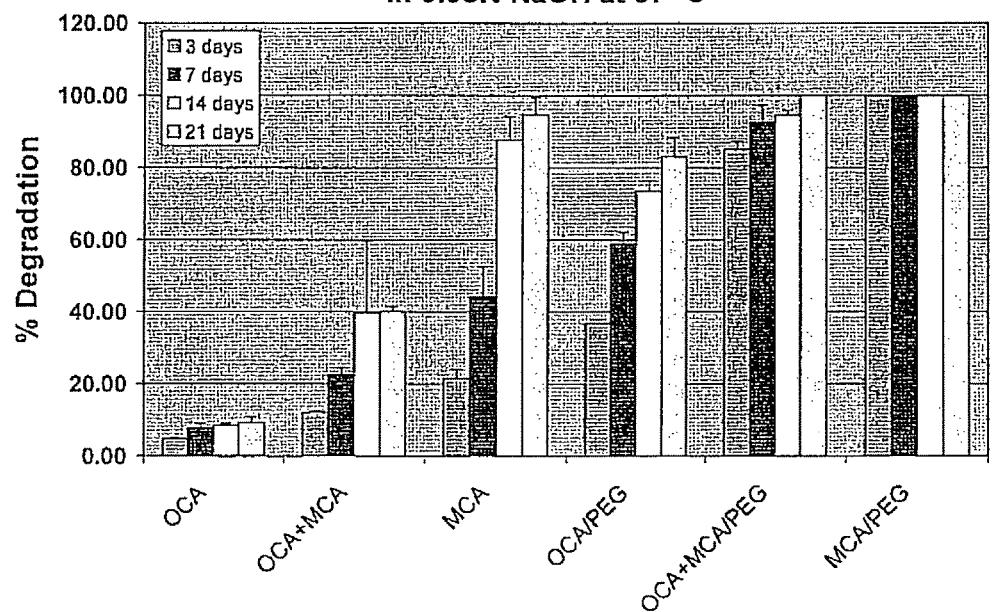
Figure 1. Degradation study of various cyanoacrylate adhesive formulations in 0.05N NaOH at 37 °C
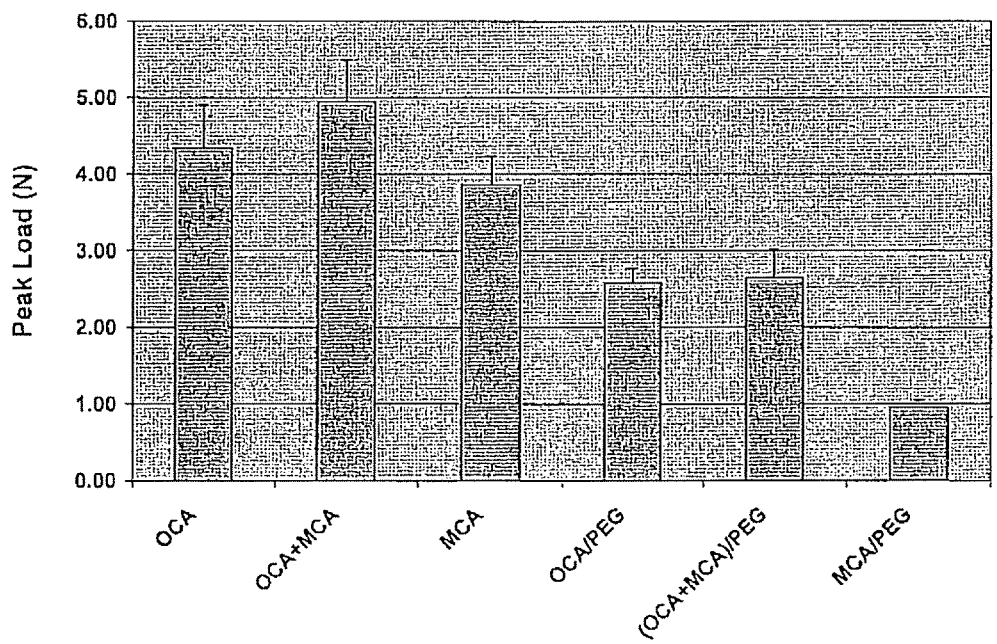
Figure 2. Bond strength test of Cyanoacrylate derivatives using rat skin (n=8)

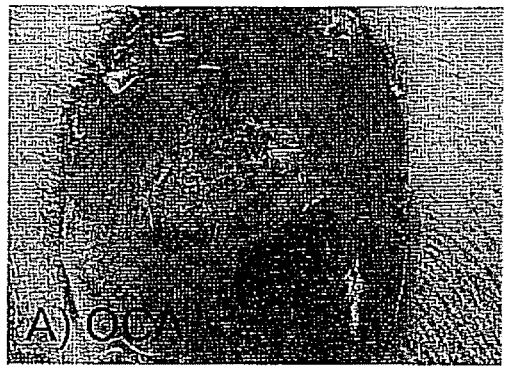
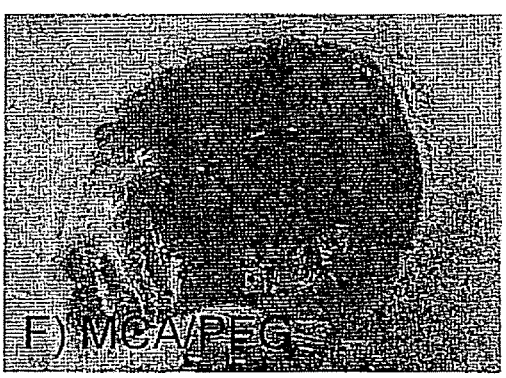
Figures 3A – 3F. Explants of various cyanoacrylate adhesives at 7 days post-surgery

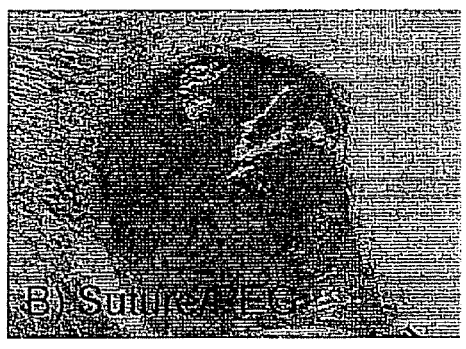
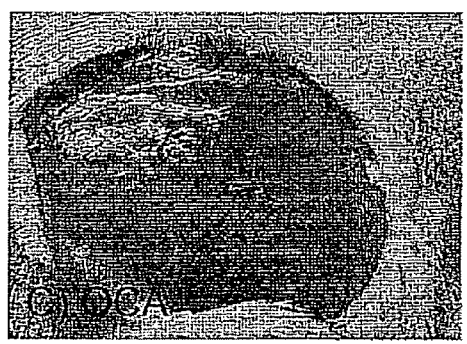
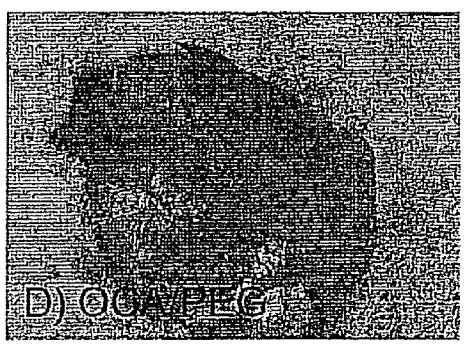
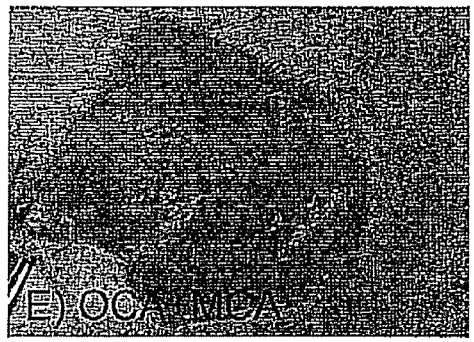
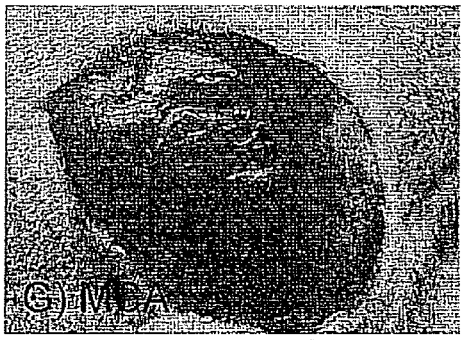
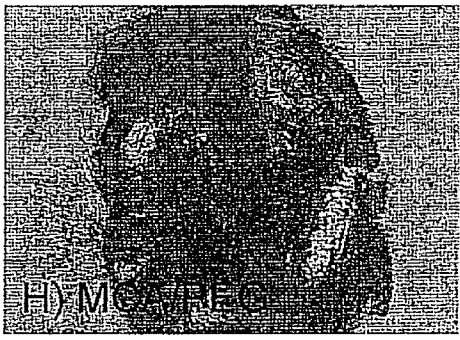
Figures 4A – 4H. Explants of various cyanoacrylate adhesives at 4 weeks post-surgery

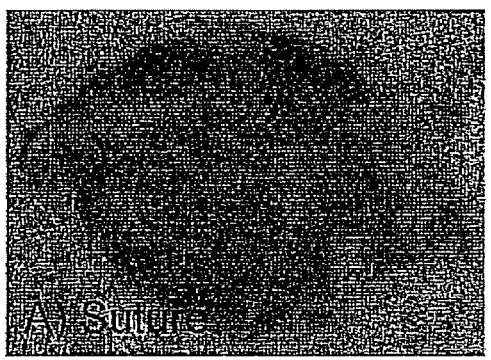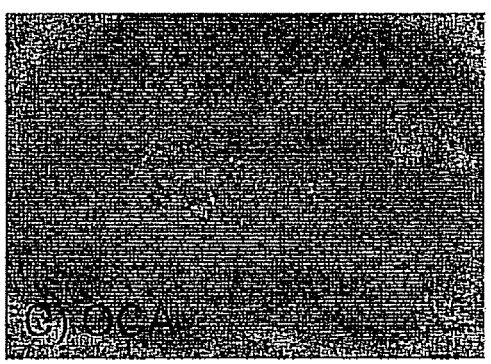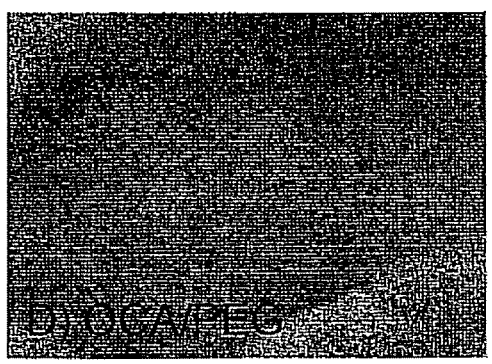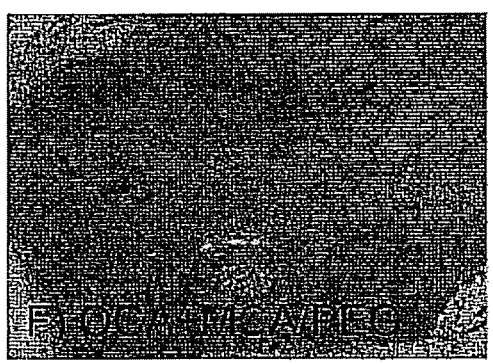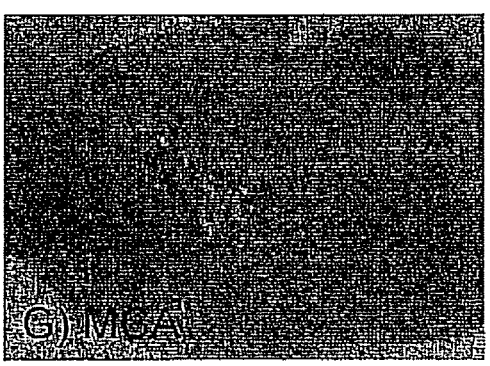
Figures 5A – 5H. Explants of various cyanoacrylate adhesives at 12 weeks post-surgery

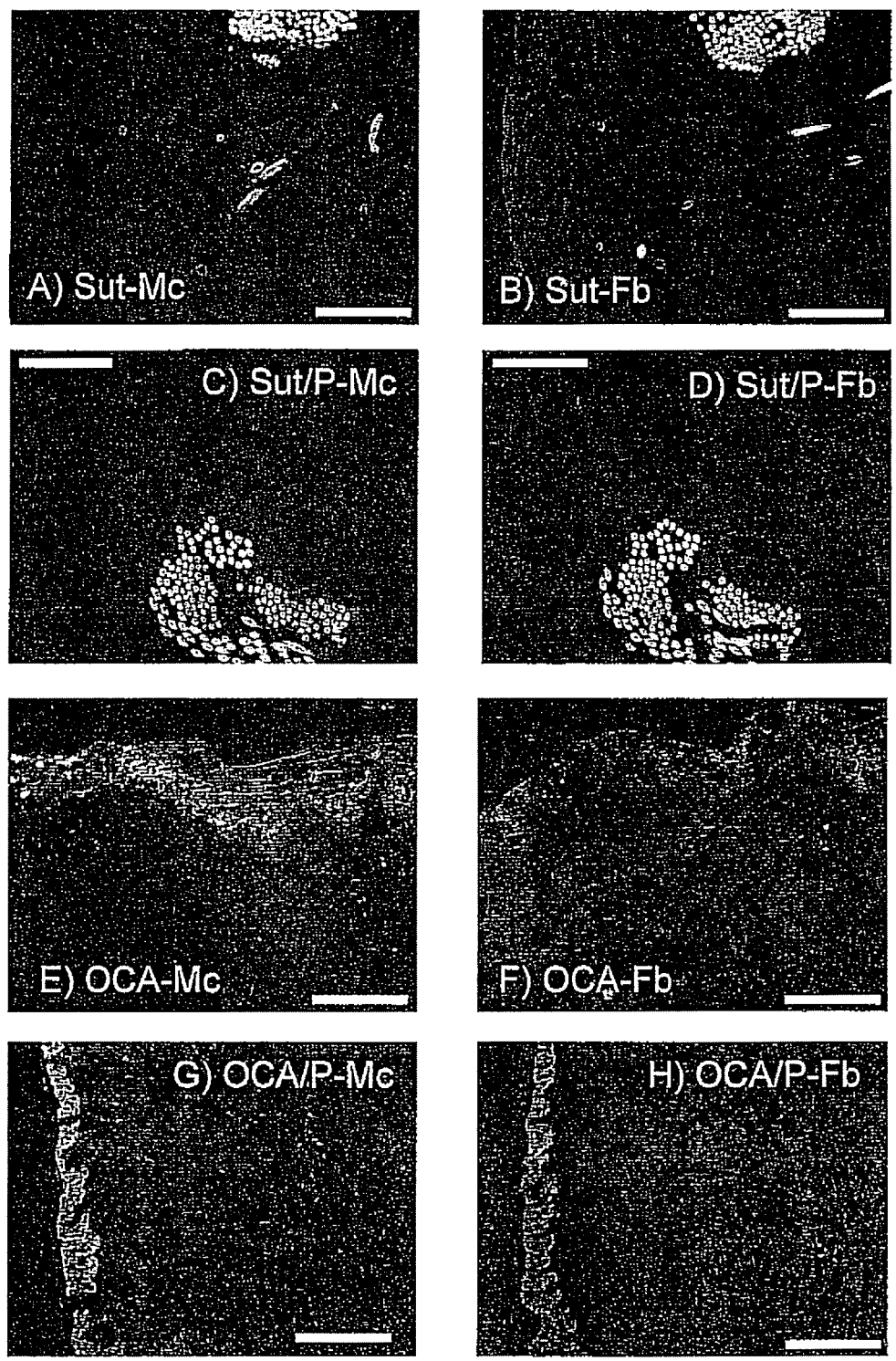
Figures 6A – 6H. Evaluation of Cellular infilteration of Cyanoacrylate implants at 7 days post-surgery by immunohistological staining
Red: Macrophage (Mc) and Fibroblast (Fb) positive cells
Blue: DAPI stained non-specific cells
Green: Cyanoacrylate adhesive

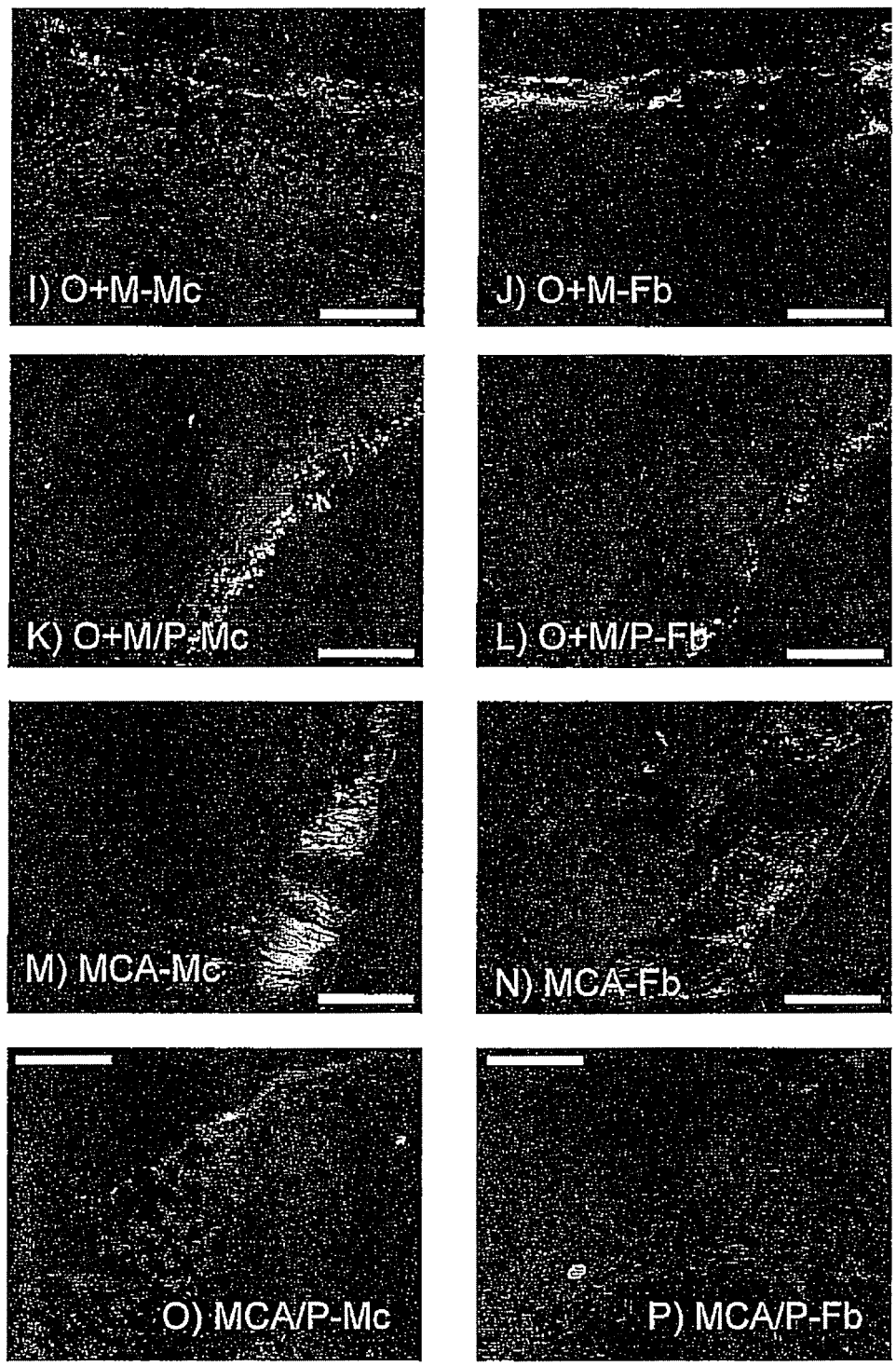
Figures 6I – 6P. Evaluation of Cellular infilteration of Cyanoacrylate implants at 7 days post-surgery by immunohistological staining
Red: Macrophage (Mc) and Fibroblast (Fb) positive cells
Blue: DAPI stained non-specific cells
Green: Cyanoacrylte adhesive

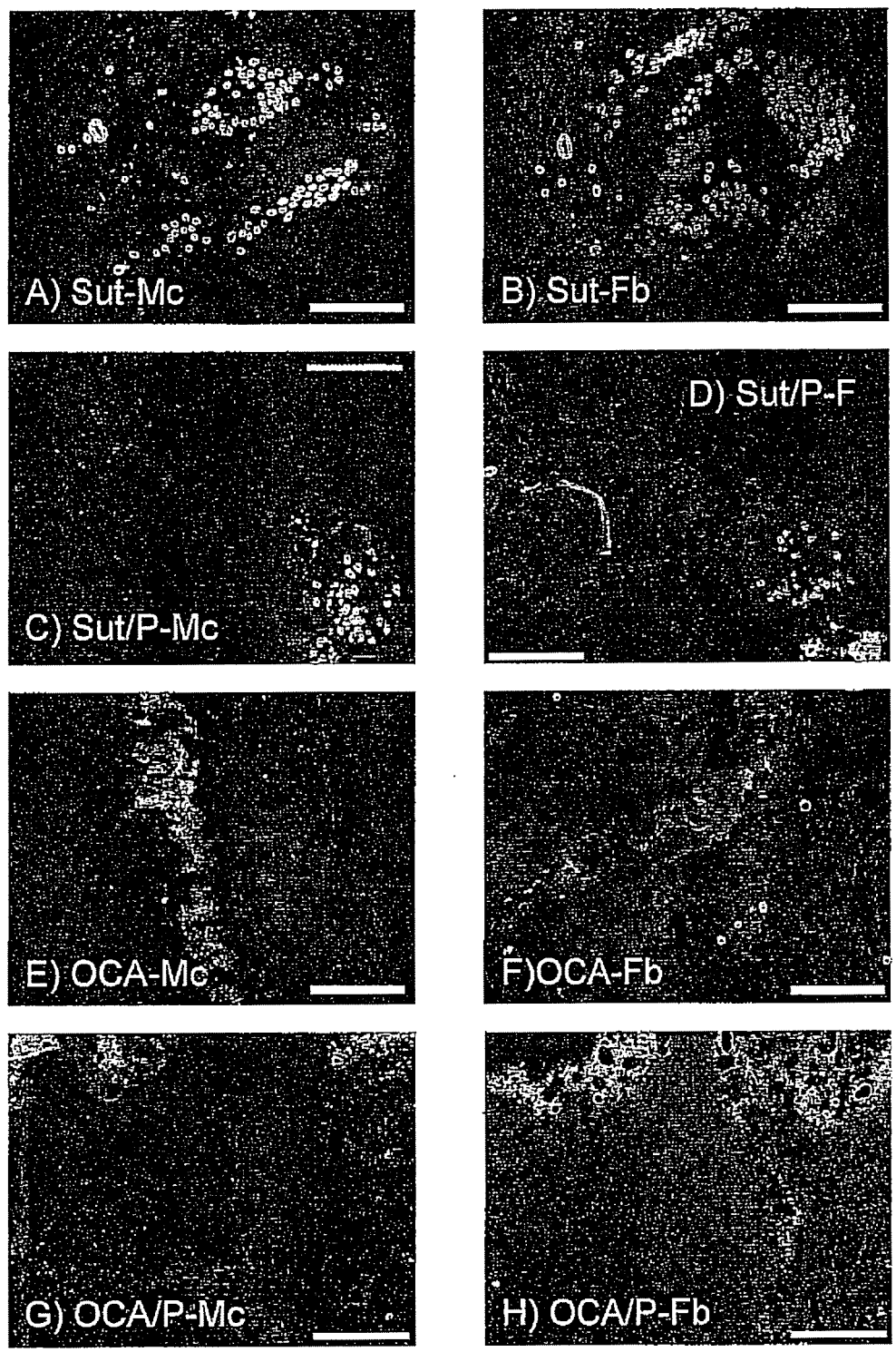
Figures 7A – 7H. Evaluation of Cellular infilteration of Cyanoacrylate implants at 4 weeks post-surgery by immunohistological staining Red: Macrophage (Mc) and Fibroblast (Fb) positive cells
Blue: DAPI stained non-specific cells
Green: Cyanoacrylte adhesive

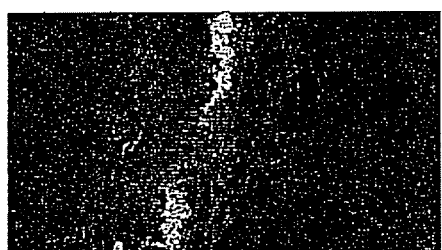
Figures 7I – 7P. Evaluation of Cellular infilteration of Cyanoacrylate implants at 4 weeks post-surgery by immunohistological staining
Red: Macrophage (Mc) and Fibroblast (Fb) positive cells
Blue: DAPI stained non-specific cells
Green: Cyanoacrylte adhesive

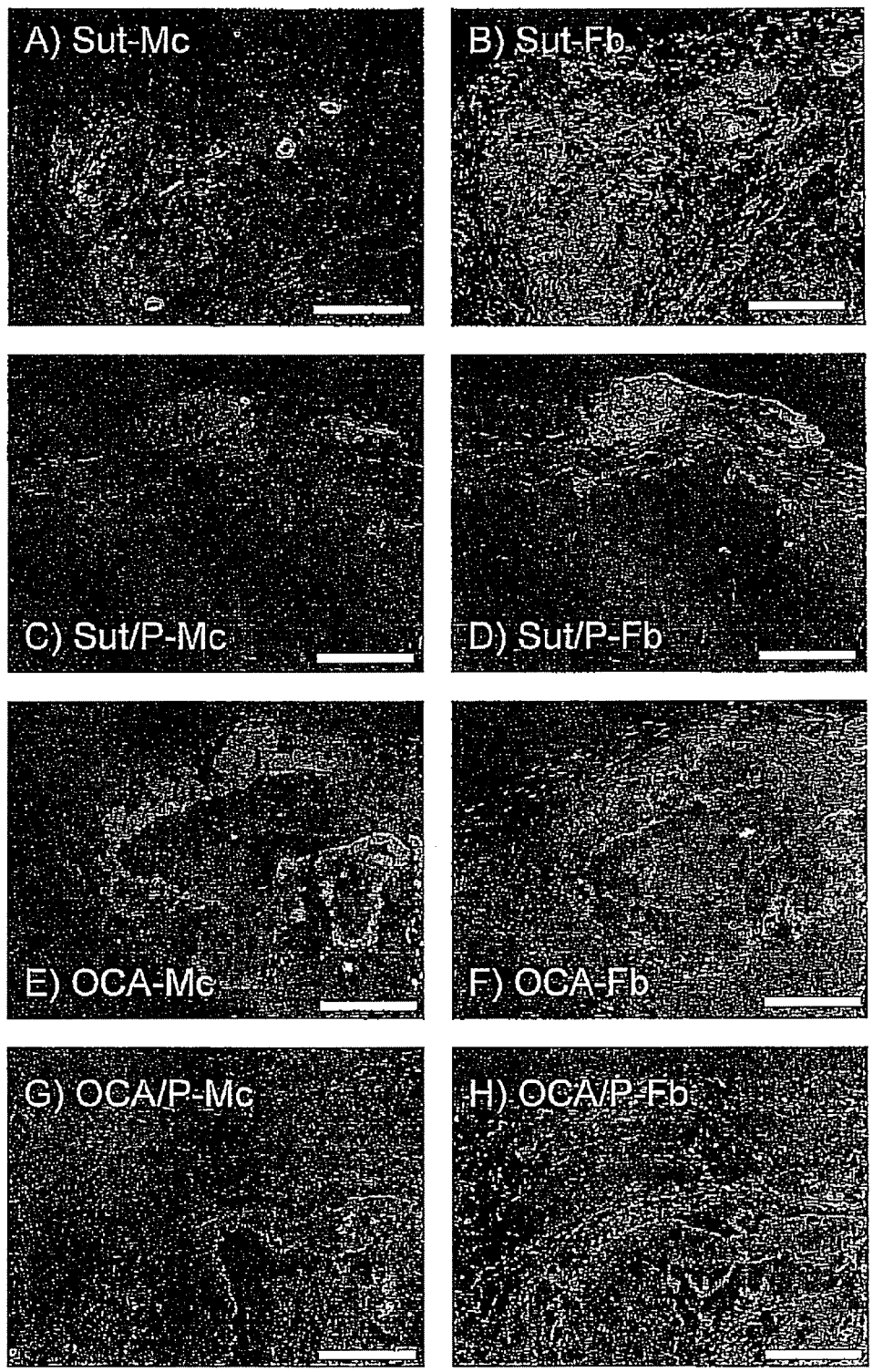
Figures 8A-H: Evaluation of Cellular infilteration of Cyanoacrylate Implants at 12 wks post-surgery by immunohistological staining
Red: Macrophage (Mc) and Fibroblast (Fb) positive cells
Blue: DAPI stained non-specific cells
Green: Cyanoacrylte adhesive

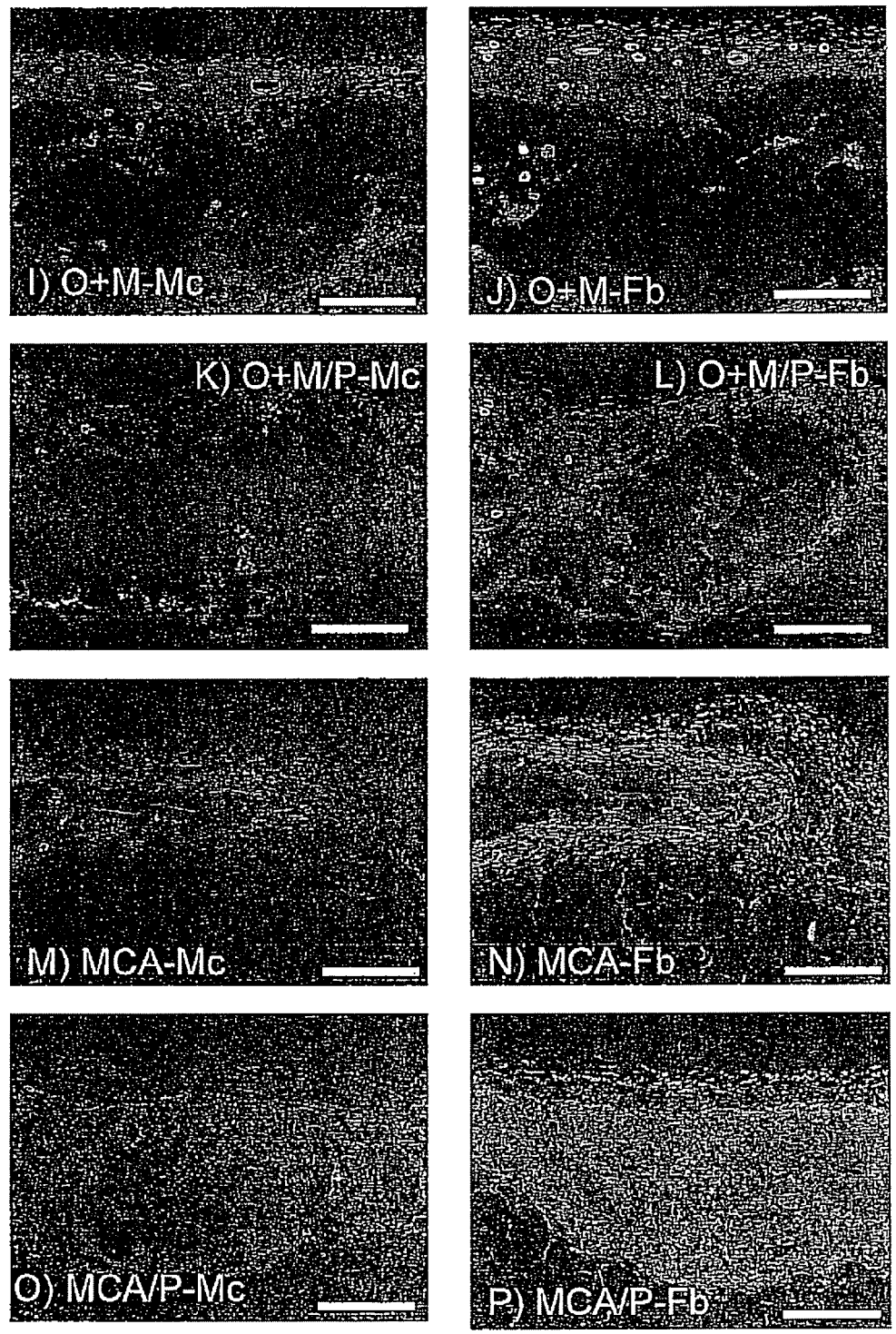
Figures 8I-P. Evaluation of Cellular infilteration of Cyanoacrylate implants at 12 wks post-surgery by immunohistological staining
Red: Macrophage (Mc) and Fibroblast (Fb) positive cells
Blue: DAPI stained non-specific cells
Green: Cyanoacrylte adhesive

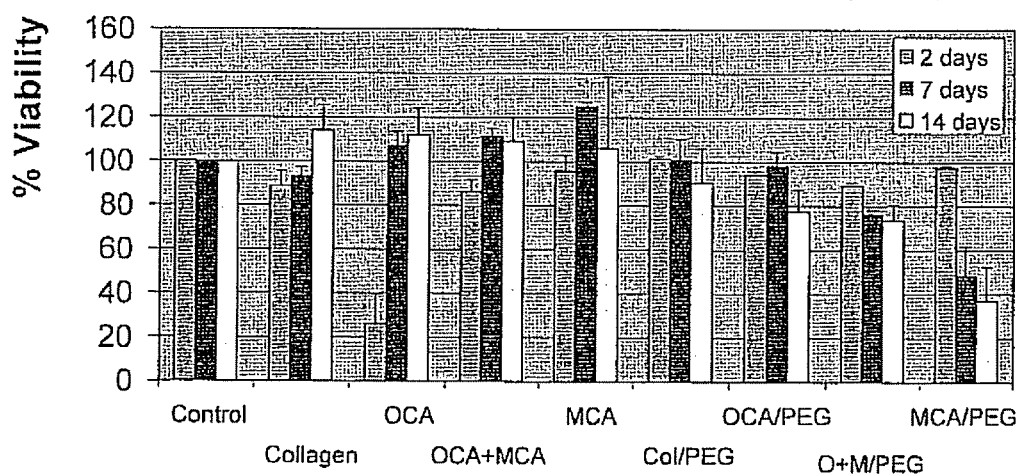
Figure 9. *In vitro* cytotoxicity of CA derivatives using Human dermal fibroblast (HDF)

E)

G)

F)

H)

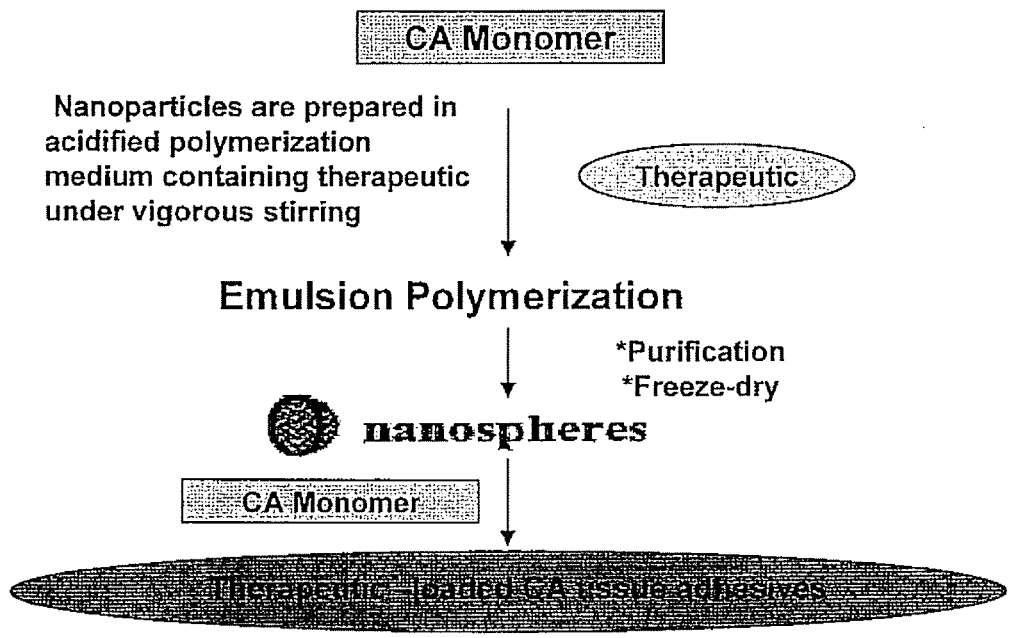
Figure 11. Preparation of therapeutic-loaded CA tissue adhesives
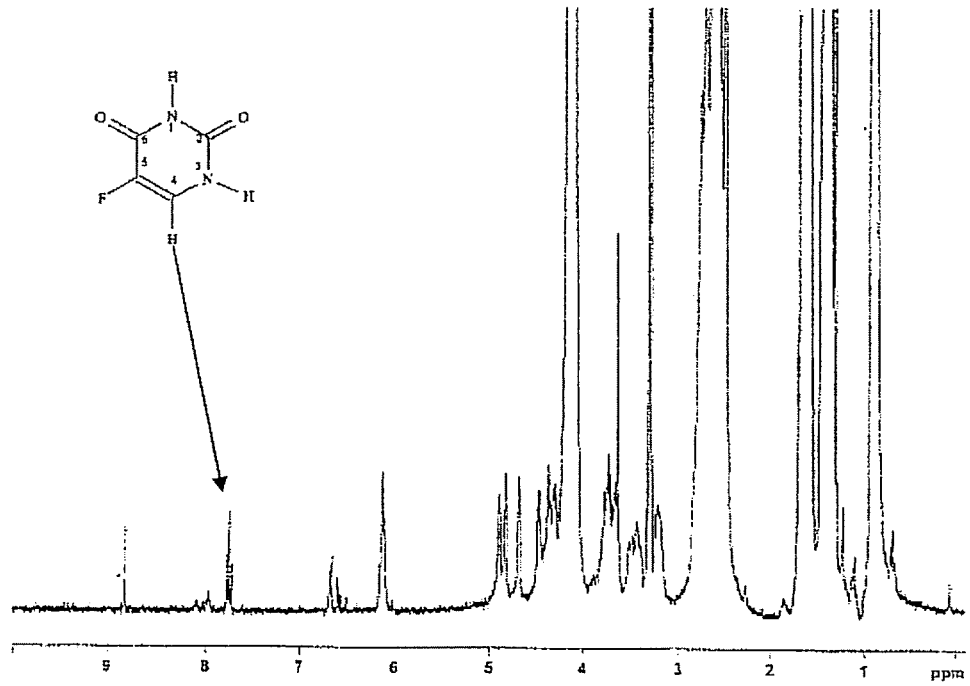
Figure 12. $^1$H-NMR spectrum of 5-FU-loaded PBCA nanoparticles nanoparticles Figures 13A-13D. Antibacterial activity test of polymyxin B-loaded PBCA particles by the agar diffusion method. A) 10 mg polymyxin B, B) 10 mg PBCA, C) 10 mg poly B/PBCA-1, and D) 10 mg poly B/PBCA-2.

CYANOACRYLATE TISSUE ADHESIVES

CROSS REFERENCE TO RELATED APPLICATIONS

This application is a continuation of U.S. patent application Ser. No. 12/742,868, which was filed on May 13, 2010 as the U.S. National Phase of PCT/US07/84607, which was filed on Nov. 14, 2007, the contents of each are incorporated by reference herein in their entirety and for all purposes.

BACKGROUND OF THE INVENTION (1) Field of the Invention

The present invention relates to tissue treatments and sealants. In particular, the present invention relates to cyanoacrylate tissue adhesives.

(2) Description of Related Art

Several different techniques have been used for internal wound closure and tissue fixation such as sutures, tapes, staples, ligating clips, and adhesives. Adhesives are easy to apply and reduce physical pain as well as the patient's anxiety associated with suture needles.

For internal applications, absorbable materials are highly preferred. Absorption eliminates the foreign body response characteristic of all permanent synthetic implants, and eliminates the need for a second surgery for material removal. The most widely used absorbable materials for internal tissue fixation and wound closure are sutures formed of degradable poly alpha-hydroxy acids, for example, polyglactin 910 (VICRYL®, Johnson and Johnson). Adhesives are particularly attractive because of their ability for simple, rapid application and curing.

Alkyl cyanoacrylate monomers have been used as tissue adhesives for several decades. Cyanoacrylate tissue adhesives are liquid monomers and can polymerize quickly on contact with tissue surface creating a thin, flexible film. This polymer film creates a mechanical barrier, which maintains a natural healing environment. Short alkyl chain cyanoacrylates such as methyl, ethyl, and isopropylcyanoacrylates were used as tissue adhesives, but because of their rapid in vivo degradation, resulting in significant tissue toxicity and inflammation, they were replaced by longer-chain cyanoacrylates such as butyl and octylcyanoacrylate. Octylcyanoacrylate has received FDA approval in 1998 and is marketed for skin wound closure after lacerations or incisions.

Cyanoacrylates offer a number of advantages, specifically as internal adhesives. Because their polymerization is initiated by functional groups found on biomolecules in tissue, their tissue bonding capability is greater than other types of adhesives. Cyanoacrylate adhesives also exhibit excellent bond strength and very rapid cure time. Cyanoacrylate esters with very short alkyl side chains (methyl and ethyl) are rapidly absorbed, but result in significant tissue toxicity. Cyanoacylate esters with longer alkyl side chains exhibit reduced toxicity, but undergo extremely slow absorption.

In order to address this limitation, several methods have been developed to accelerate degradation of cyanoacrylate adhesives. One method involves the introduction of a second ester bond during synthesis, which increases the susceptibility to hydrolysis (U.S. Pat. No. 6,620,846 to Jonn, et al.). Another method pioneered by Shalaby in U.S. Pat. Nos. 6,299,631 and 6,669,940 is the use of alkoxycyanoacrylate esters, specifically 2-methoxypropylcyanoacrylate, in combination with plasticizers of low molecular weight liquid polyesters, specifically those based on oxalic acid. Several different polyester plasticizers can be used, such as a copolyester comprising a polyethylene glycol (PEG) linked to succinate and oxalate units. Thus, the PEG is incorporated by chemical bonds into a polyester by copolymerization.

Recently, cyanoacrylate has been receiving much attention as a drug and gene delivery carrier, and anticancer drug loaded cyanoacrylate nanoparticles have been developed to treat cancer. Most drugs are either physically or chemically immiscible with cyanoacrylates. In the case of hydrophilic drugs, they cannot be miscible physically, and in the case of hydrophobic drugs, they can be miscible, but drugs which contain amine groups readily initiate cyanoacrylate polymerization. It would be desirable to deliver therapeutics to the site to which the adhesive is applied, such as antibiotics to prevent infection of a surgical site or anticancer agents to prevent cancer recurrence after surgery.

U.S. Pat. No. 6,746,667 to Badejo, et al., U.S. Pat. No. 6,942,875 to Hedgpeth, and U.S. Pat. No. 6,767,552 to Narang (all assigned to Closure Medical Co.), disclose haloprogin, an antifungal agent, mixed with 2-octylcyanoacrylate (OCA) monomer by adding haloprogin directly into OCA; and used said agent for different topical applications to remedy infections such as tenia pedis, oral fungal, and skin yeast. Direct mixing of haloprogin with the cyanoacrylate is possible because haloprogin is hydrophobic and does not contain any amine group in the structure that would initiate cyanoacrylate polymerization. Thus, such a system would not work with drugs that are hydrophilic or which have amine groups in their structure.

U.S. Pat. No. 6,086,906 to Greff, et al. (assigned to Medlogic Global Co.) discloses various antimicrobial agents mixed directly with octylcyanoacrylate, but only polyvinylpyrrolidone iodine complex was compatible with the cyanoacrylate and showed a broad spectrum of antibacterial activity. Polyvinylpyrrolidone is a polymer and has a tertiary amine group in its structure, but it is used make a complex with iodine. This tertiary amine cannot initiate cyanoacrylate polymerization.

U.S. Pat. No. 6,974,585 to Askill discloses a cyanoacrylate formulation containing mixed antibiotics (0.3% neomycin, 0.15% polymyxin B, and 0.55% bacitracin zinc). These drugs, however, form a suspension that does not mix with cyanoacrylate monomer homogeneously and they form a suspension. The formulation must be prepared in the operating room on an as needed basis and used immediately; which is typically not convenient, especially for consumer use.

Therefore, there is a need for a cyanoacrylate adhesive (1) that is readily absorbable in the body; (2) that does not cause significant tissue toxicity; (3) that can transport drug molecules effectively at a site of application for therapeutic treatment; and (4) that is a formulation that is easy to use.

BRIEF SUMMARY OF THE INVENTION

The present invention provides for tissue adhesives including cyanoacrylate and polyethylene glycol (PEG), wherein the PEG remains a polyether and wherein the tissue adhesive is bioabsorbable. The present invention provides for tissue adhesives including cyanoacrylate bulk monomer and cyanoacrylate nanoparticles containing a therapeutic therein.

The present invention further provides kits for applying tissue adhesives, including the above-described tissue adhesives and an applicator. A method is provided for applying tissue adhesives to tissue.

A method of closing an internal wound is provided by applying a tissue adhesive to a wound site, wherein the tissue adhesive includes cyanoacrylate and PEG and is bioabsorbable, allowing the wound to heal, and degrading the tissue adhesive by accelerated hydrolytic degradation due to water uptake by the PEG.

A method of sealing tissue internally is provided by applying tissue adhesive including cyanoacrylate and PEG, wherein the tissue adhesive is bioabsorbable to tissue, and sealing the tissue.

Methods are further provided of (1) administering therapeutics to tissue; (2) treating cancer; and (3) preventing infection in a wound; all of which can be performed by applying a tissue adhesive including cyanoacrylate bulk monomer and cyanoacrylate nanoparticles containing a therapeutic, and releasing the therapeutic from the cyanoacrylate nanoparticles to the tissue.

A method is provided of accelerating degradation of a cyanoacrylate tissue adhesive by adding PEG to cyanoacrylate to create a cyanoacrylate tissue adhesive, applying the cyanoacrylate tissue adhesive to tissue, and degrading the tissue adhesive by accelerated hydrolytic degradation due to water uptake by the PEG and rapidly clearing the PEG through a patient's kidneys.

Methods are also provided for making a bioabsorbable tissue adhesive and for making a therapeutic tissue adhesive.

BRIEF DESCRIPTION ON THE DRAWINGS

Other advantages of the present invention will be readily appreciated as the same becomes better understood by reference to the following detailed description when considered in connection with the accompanying drawings, wherein:

FIG. 1 is a bar graph showing a degradation study of various cyanoacrylate adhesive formulations;

FIG. 2 is a bar graph showing a bond strength test of cyanoacrylate derivatives using rat skin;

Figures 10A, 10B, 10C, 10D:
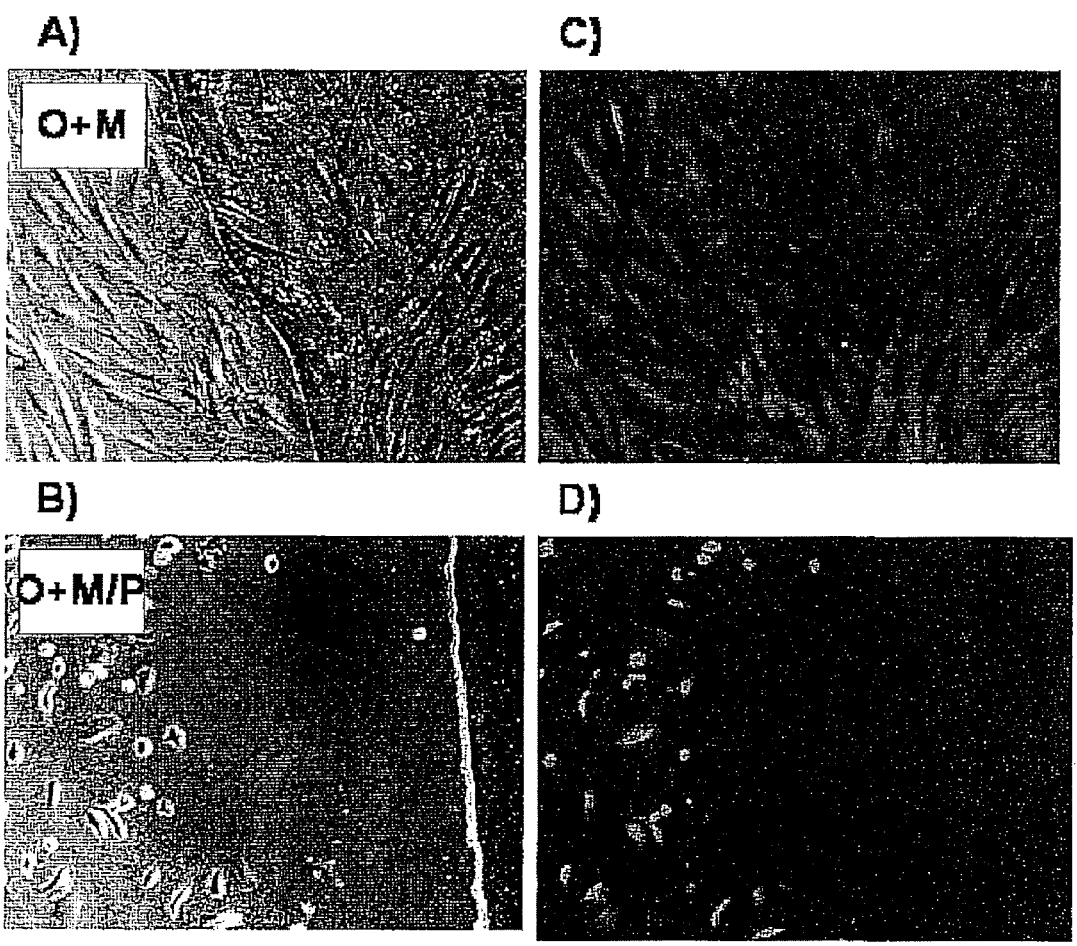
Figure 10E:
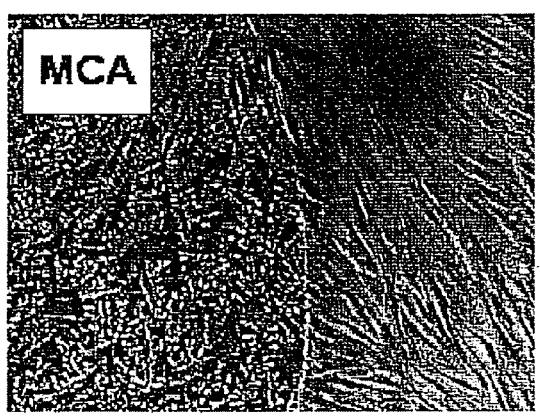
Figure 10F:
Figure 10G:
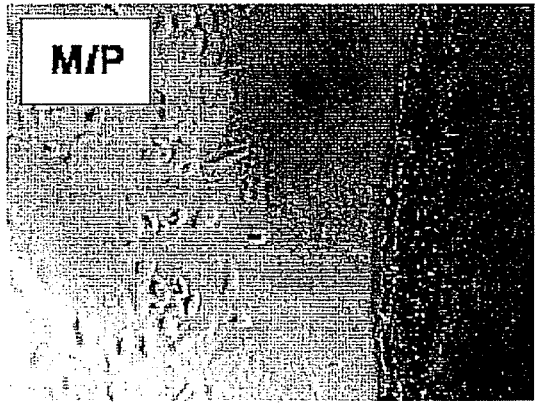
Figure 10H:

FIGS. 3 A-3F are photographs of explants of various cyanoacrylate adhesives at 7 days post-surgery;

FIGS. 4A-4H are photographs of explants of various cyanoacrylate adhesives at 4 weeks post-surgery;

FIGS. 5A-5H are photographs of explants of various cyanoacrylate adhesives at 12 weeks post-surgery;

FIGS. 6A-6P are fluorescent microscopy images evaluating cellular infiltration of cyanoacrylate implants at 7 days post-surgery by immunohistological staining, red: Macrophage (Mc) and Fibroblast (Fb) positive cells, blue: DAPI stained non-specific cells, green: cyanoacrylate adhesive;

FIGS. 7A-7P are fluorescent microscopy images evaluating cellular infiltration of cyanoacrylate implants at 4 weeks post-surgery by immunohistological staining, red: Macrophage (Mc) and Fibroblast (Fb) positive cells, blue: DAPI stained non-specific cells, green: cyanoacrylate adhesive;

FIGS. 8A-8P are fluorescent microscopy images evaluating cellular infiltration of cyanoacrylate implants at 12 weeks post-surgery by immunohistological staining, red: Macrophage (Mc) and Fibroblast (Fb) positive cells, blue: DAPI stained non-specific cells, green: cyanoacrylate adhesive;

FIG. 9 is a bar graph showing in vitro cytotoxicity of cyanoacrylate derivatives using Human dermal fibroblasts;

FIGS. 10A (OCA+MCA), 10B (OCA+MC A/PEG), 10E (MCA), and 10F (MCA/PEG) are phase contrast images showing the interface between the cyanoacrylate adhesives and the surrounding collagen films. FIGS. 10C (OCA+ MCA), 10D (OCA+MCA/PEG), 10G (MCA), and 10H (MCA/PEG) are corresponding fluorescent images showing the location of adherent cells;

FIG. 11 is a flow chart showing the preparation of therapeutic-loaded cyanoacrylate tissue adhesives;

FIG. 12 is an $^X$H-NMR spectrum of 5-FU-loaded polymyxin B-loaded polybutylcyanoacrylate (PBCA) particles; and FIGS. 13A-13D are photographs showing an antibacterial activity test of polymyxin B-loaded (PBCA) paticles by the agar diffusion method, 13A shows 10 mg polymyxin B, 13B shows 10 mg PBCA, 13C shows 10 mg poly B/PBCA-1 (equivalent to 1.93 mg of free polymyxin B), and 13D shows 10 mg poly B/PBCA-2 (equivalent to 1.24 mg of free polymyxin B).

DETAILED DESCRIPTION OF THE INVENTION

The present invention provides novel cyanoacrylate tissue adhesives. In a first embodiment of the invention, a bioabsorbable cyanoacrylate tissue adhesive is formed from a composition including cyanoacrylate and polyethylene glycol (PEG). A second embodiment of the invention further provides a composition including cyanoacrylate bulk monomer and cyanoacrylate nanoparticles containing an effective amount of a therapeutic therein.

The novel bioabsorbable cyanoacrylate tissue adhesive formulation is a blend of cyanoacrylate (also referred to herein as CA) and a low molecular weight polyether. The polyether can be any low molecular weight homopolymer such as polyethylene glycol (PEG) or various di- and tri-block copolymers of polyethylene glycol and polypropylene glycol, such as, but not limited to, PLURONIC® (BASF). Most preferably, the polyether is PEG.

The bioabsorbable cyanoacrylate adhesives described herein are shown to have an accelerated degradation rate compared to that of an adhesive of a pure cyanoacrylate composition. Unlike compositions described above in the prior art, the present invention is not a copolymer of cyanoacrylate and PEG, but rather the PEG remains a polyether. Polyethers, including PEG, are essentially non-degradable in the human body. However, they are highly water-soluble and rapidly cleared through the kidneys. Because of its hydrophilic and water soluble properties, PEG accelerates cyanoacrylate degradation by increasing water uptake into the cured adhesive, accelerating hydrolytic degradation. PEG is also known to act as a plasticizer, increasing the viscosity of the adhesive.

Two potentially useful formulations have been developed as preferred embodiments. The first formulation, MCA/ PEG, is a blend of methoxyisopropylcyanoacrylate (MCA) with a low molecular weight PEG (MW=600) at 85:15 (v/v % MCA/PEG) ratio. A thin film of MCA/PEG applied to an in viva incision created in the rat hind limb muscle is essentially degraded in 12 weeks, and degraded more extensively than MCA alone. This is the most rapidly degrading formulation developed. OCA+MCA/PEG is a second potentially useful formulation, consisting of a 50:50 v/v % mixture of octylcyanoacrylate (OCA) and MCA formulated with PEG at a 85:15 (v/v % CA/PEG) ratio. While exhibiting slower degradation than MCA/PEG, this formulation shows accelerated degradation relative to a composition of OCA+ MCA (50:50 v/v %) without PEG. This formulation also exhibits significantly increased tissue bond strength relative to MCA/PEG. While the addition of PEG weakens the bond strength, OCA fortifies the bond strength.

The bioabsorbable cyanoacrylate adhesives can be used in many different applications, such as, but not limited to, cardiac surgery, general wound closure, hernia surgery, artheroscopic surgery, endoscopic surgery, and any type of major or minor surgery. Further, the bioabsorbable cyanoacrylate adhesive can be used as an internal sealant, for such applications as sealing tissue together, among others.

In other words, the present invention provides for a method of sealing tissue internally, including the steps of applying the tissue adhesive of the first embodiment to tissue, and sealing the tissue. The present invention also provides for a method of closing an internal wound, including the steps of applying the tissue adhesive of claim of the first embodiment to a wound site, allowing the wound to heal, and degrading the tissue adhesive by accelerated hydrolytic degradation due to water uptake by the PEG.

In use, the bioabsorbable cyanoacrylate adhesive is applied to the desired tissue area as a liquid which then polymerizes upon contact with tissue. The polymerized patch of bioabsorbable cyanoacrylate adhesive allows the tissue to heal properly. Over time, water is drawn into the adhesive, causing it to degrade. The components of the adhesive then are cleared from the body.

Therefore, the present invention provides for a method of accelerating degradation of a cyanoacrylate tissue adhesive, including the steps of adding PEG to cyanoacrylate to create a cyanoacrylate tissue adhesive, applying the cyanoacrylate tissue adhesive to tissue, and degrading the tissue adhesive by accelerated hydrolytic degradation due to water uptake by the PEG and rapidly clearing the PEG through a patient's kidneys.

The second embodiment of the invention pertains to a method for creating stable formulations of therapeutic-containing cyanoacrylate adhesives. Hereinafter, the therapeutic can also be referred to as a drug. The method involves the entrapment of the therapeutics in polyalkylcyanoacrylate nanoparticles. Essentially, this process creates a stable coating of polymerized cyanoacrylate around the therapeutic molecule/compound. Once purified and dried, the therapeutic-loaded cyanoacrylate nanoparticles can be homogeneously mixed with bulk cyanoacrylate monomer without initiating polymerization. Once the liquid adhesive is applied to tissue and polymerizes, the cyanoacrylate nanoparticles are degraded by hydrolysis of the cyanoacrylate ester, becoming water soluble cyanoacrylic acid and releasing free therapeutic at the surface of the wound or tissue. Dosing can be controlled by the amount of nanoparticles initially loaded. The choice of cyanoacrylate alkyl chain length and its effect on degradation rate can also be used to control dosing.

Complex mixtures of multiple therapeutics such as those used in commercial antibiotic ointments (e.g. polysporin, which contains polymyxin B, Bacitracin, and Gramacidin as antibiotics and lidocaine as local anesthetics) can be readily created by mixing multiple types of therapeutic-loaded nanoparticles with the adhesive. Primary applications include antibiotic delivery for reduction of wound infection and delivery of anticancer chemotherapeutic drugs to wound sites following removal of malignant tissue. Other applications include nicotine or glucose delivery in a patch of the polymerized cyanoacrylate adhesive. In other words, a patch can be made out of the cyanoacrylate liquid adhesive that contains a therapeutic, and the patch can be applied to a desired area of tissue. When the patch is applied to the tissue, it is degraded as described above and releases the therapeutic. Such patches can be controlled-release according to the methods of controlling dosing described above. Table I below shows various therapeutics that can be loaded in CA nanoparticles for topical application. The therapeutics listed therein are not exhaustive, and any suitable therapeutic can be loaded into CA nanoparticles for delivery through the cyanoacrylate adhesive.

TABLE I

Drugs for use in topical application

| Antibacterial agents | Antifungal agents | Anticancer agents | Antiinflammatory drugs |
|---|---|---|---|
| Polymyxin B sulfate | Terb marine | 5-Fluorouracil | Ibuprofen |
| Neomycin sulfate | Clotrimazole | Doxorubicin | Ketoprofen |
| Gentamycin sulfate | Ketokonazole | Paclitaxel | Dexamethas one |
| Gramicidin | Nystatin | | Predisolone |
| Zinc Bacitracin | Amphotericin B | | |
| Hydroxyquinolone | | | |

For example, the nanoparticles can contain an anticancer agent. Thus, the present invention provides for a method of treating cancer, including the steps of applying a tissue adhesive including cyanoacrylate bulk monomer and cyanoacrylate nanoparticles containing an effective amount of an anticancer agent, releasing the anticancer agent from the cyanoacrylate nanoparticles to the tissue, and treating cancer.

The nanoparticles can also contain an antibiotic. Thus, the present invention provides for a method of preventing infection in a wound, including the steps of applying a tissue adhesive including cyanoacrylate bulk monomer and cyanoacrylate nanoparticles containing an effective amount of an antibiotic therapeutic to a wound, releasing the antibiotic therapeutic from the cyanoacrylate nanoparticles to the tissue, and preventing infection in the wound.

The second embodiment with therapeutic-loaded CA nanoparticles can be practiced in combination with the first embodiment, i.e., a bioabsorbable CA and PEG bulk monomer. Thus, the therapeutic-loaded nanoparticles can effectively be released internally or at an outer site where quick degradation of the CA adhesive is desired. This is especially desirable where a therapeutic needs to be delivered to an internal surgical site. Therapeutic release from nanoparticles in cyanoacrylate adhesive can be substantially accelerated by the incorporation of PEG within the cyanoacrylate adhesive. Increased water uptake mediated by PEG can accelerate nanoparticle degradation and therapeutic release from nanoparticles, as well as increase the permeability of the adhesive to the therapeutic, thus facilitating its diffusion from the adhesive into the surrounding tissue.

In use, the therapeutic-containing cyanoacrylate adhesive is applied as a liquid to the desired tissue area, which then polymerizes into a patch upon contact with the tissue. Alternatively, the therapeutic-containing cyanoacrylate adhesive is already in a patch form as described above and applied as such to tissue. Over time, the cyanoacrylate nanoparticles of the patch release the therapeutic at the surface of the tissue as the nanoparticles degrade. Thus, not only does the tissue heal by application of the cyanoacrylate adhesive, but the therapeutic also promotes healing and/or prevention of further disease.

Several kits are provided for the present invention. A kit generally includes an applicator containing the cyanoacrylate bulk monomer composition. A kit for the second embodiment of the invention further includes the therapeutic-loaded nanoparticles. The therapeutic-loaded nanoparticles can be directly mixed in with the cyanoacrylate bulk monomer inside the applicator. A compartment containing the cyanoacrylate tissue adhesive inside the applicator can be activated when needed, and the cyanoacrylate tissue adhesive flows out of the applicator to be applied to tissue. A sponge can be included on the tip of the applicator for easy application.

It is also envisioned that the therapeutic-loaded nanoparticles can be contained in a compartment within the applicator, separate from the cyanoacrylate bulk monomer. For example, a sponge tip of the applicator can contain an antibiotic in a water-based solution or micelle and a separate compartment can contain the cyanoacrylate bulk monomer. When the compartment is opened or activated, the cyanoacrylate bulk monomer flows through the sponge tip and picks up the antibiotic before flowing to a surface of the sponge. Thus, when the sponge surface is applied to a wound, the adhesive contains both the bulk cyanoacrylate monomer and the antibiotic. Another applicator can contain two compartments, one with bulk cyanoacrylate monomer, and one with a therapeutic. For example, the compartments can be at opposite ends in a single tube, or side by side vertically. The compartment with the therapeutic can be opened or activated to apply the therapeutic first, and then the compartment with the bulk cyanoacrylate monomer can be opened to apply the adhesive.

Individual applicators can be packaged separately to maintain sterile conditions. For example, each applicator can be packaged in plastic or any other suitable enclosing material. Multiple applicators can then be packaged in a box for shipping.

The compounds of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compound and can be administered alone or as an active ingredient in combination with pharmaceutically acceptable carriers, diluents, adjuvants and vehicles. The compounds can be administered in any suitable way. The patients being treated are warm-blooded animals and, in particular, mammals including human beings. The pharmaceutically acceptable carriers, diluents, adjuvants and vehicles as well as implant carriers generally refer to inert, nontoxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention with the CA nanoparticles containing therapeutics parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity of the therapeutics can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the therapeutics contained in the CA nanoparticles of the present invention can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925, 678; 4,487,603; 4,486,194; 4,447,233; 4,447,224; 4,439,196; and 4,475,196. Many other such implants, delivery systems, and modules are well known to those skilled in the art.

While specific embodiments are disclosed herein, they are not exhaustive and can include other suitable designs and systems that vary in designs, methodologies, and transduction systems (i.e., assays) known to those of skill in the art. In other words, the examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Experimental Methods and Results

A series of experiments have been performed to evaluate the efficacy of cyanoacrylate adhesive formulations incorporating PEG. Throughout all experiments, PEG (MW=600) was added to cyanoacrylates at a 85:15 (v/v Cyanoacrylate/PEG) ratio. Three cyanoacrylate compositions were used: octylcyanoacrylate (OCA), a 50:50 mixture of octylcyanoacrylate and methoxyisopropylcyanoacrylate (OCA:MCA) and methoxyisopropylcyanoacrylate (MCA). Pure cyanoacrylate formulations were used throughout as controls for comparison to experimental formulations containing PEG.

1. In Vitro Degradation Study

In vitro accelerated degradation studies have been performed to evaluate the degradation rate of various cyanoacrylate adhesives formulated with PEG and without PEG. 20 μl of cyanoacrylate (CA) derivatives and CA derivatives/PEG (MW=600) formulations were spread as a thin layer on the glass microscope slides and allowed to cure overnight at room temperature. The resulting thin films (1.5 cm×1.5 cm) were weighed ($W_0$) and incubated in 10 ml 0.05N NaOH solution at 37° C. The films were collected at 3, 7, 14, and 21 days and washed with distilled water two times. The washed films were freeze-dried and weighed ($W_1$) (n=3). Percent degradation was then calculated from the following formula:

$$\% \text{ Degradation of cyanoacrylate derivatives} = (W_o - W_t)/W_o \times 100 \quad (1)$$

FIG. 1 shows % degradation of various cyanoacrylate derivatives in 0.05 N NaOH solution. Formulations based on cyanoacrylate monomers with short alkyl side chains (MCA) exhibited significantly increased degradation relative to those based on monomers with long alkyl side chains (OCA), consistent with previous reports in the literature. Formulations comprising mixture of OCA:MCA (50:50) exhibited intermediate levels of degradation relative to each monomer. The addition of 15% PEG significantly increased in vitro degradation rate of all cyanoacrylate formulations.

2. Tissue Bond Strength Study

Rat skin samples were harvested from the backs of Sprague-Dawley rats and cut into strips (1 cm in width, 5 cm in length). The strips were cut in half and 2 μl of various cyanoacrylate formulations were applied to each side of cut edges to glue them. The glued strips were incubated overnight at 4° C. in humidified chamber to allow them to cure. Bond strength of samples (n=4) was tested using MTS Synergie 100 (MTS System Corporation). FIG. 2 shows the bond strength of various cyanoacrylate formulations. The addition of PEG significantly decreased tissue bond strength relative to each corresponding formulation of cyanoacrylate. The MCA/PEG formulation exhibited significantly reduced tissue bond strength relative to OCA and OCA/MCA formulations including PEG.

3. Immunohistochemical (IHC) Staining for Evaluation of In Vivo Biocompatibility Small surgical incisions (0.2 cm in depth, 1 cm in length) were made in both hind limb muscles of adult Sprague-Dawley rats (n=4). One incision was closed by 1 drop of various cyanoacrylate formulations dispensed through a surgical syringe needle (25 G) and the other was closed by absorbable suture (VICRYL, Ethicon) with and without injection of equivalent volumes of PEG included in cyanoacrylate formulations as controls. In order to ensure proper identification of the injury sites, a single non-absorb-able suture was placed adjacent to each repaired incision site.

At 7 days, 4 weeks, and 12 weeks post-surgery, tissue explants containing the repaired incision sites and surrounding muscle tissue were retrieved. The explants were photographed to document the macroscopic tissue response to the various cyanoacrylate formulations and suture controls (FIGS. 3A-3H (7 days), 4A-4H (4 weeks), and 5A-5H (12 weeks)). Identification of specific cells types associated with wound healing and inflammation was performed by histological sectioning and immunohistochemical (IHC) staining. Tissue explants were embedded in Optimal cutting temperature (OCT) compound and sectioned perpendicular to the surface of the repaired muscle tissue. Sections (0.6 um thick) were transferred to glass microscope slides, fixed with methanol, permeabilized with 0.025% Triton in PBS solution, and stained with primary antibodies directed against vimentin (fibroblasts) and rat macrophages, and Alexa-594 conjugated secondary antibodies. DAPI mounting media was used to counterstain all cellular nuclei. Samples were imaged by fluorescence microscopy (FIGS. 6A-6P, 7A-7P, 8A-8P). Specific cell types are identified in red, sutures and various cyanoacrylate adhesives are shown in green, and cellular nuclei are shown in blue. Tables II, III, and IV below summarize macroscopic and histological observations of the biocompatibility and degradation of various cyanoacrylate formulations at 7 days, 4 weeks, and 12 weeks post-surgery, respectively.

TABLE II

Evaluation of biocompatibility of various cyanoacrylate adhesives at 7 days post-surgery

| Sample | Rat No. | Degree of inflammation | Vessel formation | Degree of degradation | No. of macrophages | No. of fibroblasts |
|---|---|---|---|---|---|---|
| Suture | 1 | no | no | no | ** | ** |
|  | 2 | no | no | no | ** | ** |
|  | 3 | * | no | no | ** | ** |
|  | 4 | no | no | no | ** | ** |
| Sut/PEG | 1 | no | no | no | ** | ** |
|  | 2 | no | no | no | *** | ** |
|  | 3 | no | no | no | ** | ** |
|  | 4 | no | no | no | *** | ** |
| OCA | 1 | no | no | no | ** | *** |
|  | 2 | no | no | no | *** | **** |
|  | 3 | * | no | no | **** | *** |
|  | 4 | ** | ** | no | ***** | *** |
| OCA/PEG | 1 | * | * | no | * | *** |
|  | 2 | * | * | no | *** | *** |
|  | 3 | * | * | no | *** | *** |
|  | 4 | * | no | no | **** | *** |
| OCA + MCA | 1 | no | no | no | * | * |
|  | 2 | no | no | no | * | * |
|  | 3 | no | no | no | * | * |
|  | 4 | no | no | no | ** | ** |

TABLE II-continued

Evaluation of biocompatibility of various cyanoacrylate adhesives at 7 days post-surgery

| Sample | Rat No. | Degree of inflammation | Vessel formation | Degree of degradation | No. of macrophages | No. of fibroblasts |
|---|---|---|---|---|---|---|
| OCA + MCA/ PEG | 1 | no | * | no | *** | ** |
| | 2 | no | no | no | ** | * |
| | 3 | no | no | no | ** | * |
| | 4 | no | no | no | ** | * |
| MCA | 1 | no | no | no | * | * |
| | 2 | no | no | no | ** | * |
| | 3 | no | no | no | *** | * |
| | 4 | no | no | no | *** | ** |
| MCA/PEG | 1 | no | no | no | * | * |
| | 2 | no | no | no | ** | * |
| | 3 | no | no | no | ** | * |
| | 4 | * | no | no | *** | **** |

TABLE III

Evaluation of biocompatibility of various cyanoacrylate adhesives at 4 weeks post-surgery

| Sample | Rat No. | Degree of inflammation | Vessel formation | Degree of degradation | No. of macrophages | No. of fibroblasts |
|---|---|---|---|---|---|---|
| Suture | 1: Dead | | | | | |
| | 2 | no | no | no | ** | ** |
| | 3 | no | no | no | ** | ** |
| | 4 | no | no | no | ** | ** |
| Sut/PEG | 1 | no | no | no | ** | ** |
| | 2 | no | no | no | ** | ** |
| | 3 | no | no | no | ** | ** |
| | 4 | no | no | no | ** | ** |
| OCA | 1 | * | no | no | *** | **** |
| | 2 | ** | * | no | *** | **** |
| | 3 | * | no | no | *** | *** |
| | 4 | ** | * | no | **** | **** |
| OCA/PEG | 1 | *** | | no | *** | **** |
| | 2 | *** | | no | *** | **** |
| | 3 | * | no | no | ** | ** |
| | 4 | *** | | no | *** | **** |
| OCA + MCA | 1: Dead | | | * | | |
| | 2 | no | no | * | ** | * |
| | 3 | no | no | * | ** | * |
| | 4 | no | no | * | * | * |
| OCA + MCA/PEG | 1 | no | no | ** | *** | ** |
| | 2 | no | no | ** | ** | * |
| | 3 | no | no | ** | ** | * |
| | 4 | no | no | ** | ** | * |
| MCA | 1 | no | no | ** | ** | ** |
| | 2 | no | no | ** | * | * |
| | 3 | no | no | ** | ** | * |
| | 4 | no | no | ** | * | * |
| MCA/PEG | 1 | no | no | *** | ** | * |
| | 2 | no | no | *** | * | * |
| | 3 | no | no | *** | * | * |
| | 4 | no | no | *** | ** | * |

TABLE IV

Evaluation of biocompatibility of various cyanoacrylate adhesives at 4 weeks post-surgery

| Sample | Rat. No. | Degree of inflammation | Vessel formation | Degree of degradation | No. of macrophages | No. of fibroblasts |
|---|---|---|---|---|---|---|
| Suture | 1: Dead | | | | | |
| | 2 | no | no | Degraded | ** | ** |
| | 3: Dead | | | | | |
| | 4 | no | no | Degraded | * | ** |

TABLE IV-continued

Evaluation of biocompatibility of various cyanoacrylate adhesives at 4 weeks post-surgery

| Sample | Rat. No. | Degree of inflammation | Vessel formation | Degree of degradation | No. of macrophages | No. of fibroblasts |
|---|---|---|---|---|---|---|
| Sut/PEG | 1 | no | no |  | * | ** |
|  | 2 | no | no | Degraded | 0 | ** |
|  | 3 | no | no |  | * | * |
|  | 4 | no | no | Degraded | 0 | ** |
| OCA | 1 | no | no | * | ** | **** |
|  | 2 | no | no | * | *** | *** |
|  | 3 | * | * | * | * | * |
|  | 4 | no | no | * | * | ** |
| OCA/PEG | 1 | ** | * | * | *** | **** |
|  | 2 | * | * | * | *** | *** |
|  | 3 | no | no | * | ** | *** |
|  | 4 | no | no | * | *** | *** |
| OCA + MCA | 1: Dead |  |  |  |  |  |
|  | 2 | no | no | ** | ** | ** |
|  | 3: Dead |  |  |  |  |  |
|  | 4 | no | no | ** | ** | ** |
| OCA + MCA/PEG | 1 | no | no | *** | * | ** |
|  | 2 |  |  |  | ** |  |
|  | 3 | no | no | *** | ** | ** |
|  | 4 | no | no | *** | *** | ** |
| MCA | 1 | no | no | *** | ** | ** |
|  | 2 | no | no | *** | * | ** |
|  | 3 | no | * | *** | 0 | * |
|  | 4 | no | no | ** | 0 | * |
| MCA/PEG | 1 | no | no | ***** | * | * |
|  | 2 | no | no | ***** | * | * |
|  | 3 | no | no | ***** | * | * |
|  | 4 | no | no | ***** | * | ** |

At 7 days post-surgery, macroscopic analysis of tissue explants revealed mild inflammation and swelling in response to OCA (2 of 4 rats) and OCA/PEG (all 4 rats) formulations. Suture controls and formulations based on OCA/MCA and MCA both with and without PEG appeared well integrated with the surrounding tissue. Suture controls showed little change at 4 weeks and were substantially degraded by 12 weeks. OCA and OCA/PEG samples exhibited minimal degradation at 4 or 12 weeks. Samples of OCA/MCA and MCA-based formulations exhibited progressive degradation at 4 and 12 weeks, with MCA formulations showing the greatest degree of degradation. Inclusion of PEG in OCA/MCA and MCA formulations resulted in increased degradation relative to pure cyanoacrylate formulations. These observations parallel the results of the in vitro degradation analysis with the degree of degradation proceeding in the order MCA/PEG>MCA OC A+MC A/PEG>OC A-1-MC A>OC Al PEG>OCA. These results were further confirmed by visualization of the various formulations in the histological analysis described below.

Histological analysis demonstrated that all implant materials promoted the accumulation of an increased number of cells relative to uninjured muscle tissue, which exhibits low cellularity. This cellular capsule varied in thickness as a function of the implant material and formulation. In general, macrophages were concentrated at the surface of all implants, surrounded by fibroblasts. OCA-based formulations were encapsulated by substantially thicker cell layers as compared to MCA and OCA/MCA formulations at both 7 day and 4 week time points.

4. In Vitro Cytotoxicity of CA Derivatives on Human Dermal Fibroblast (HDF) Cells 2 μl of various CA formulations were applied on thin collagen films in 12 well plates and allowed to polymerize completely overnight at room temperature. One ml of Dulbecco's Minimal Essential Medium (DMEM) including 10% Serum and 1% Penicillin/Streptomycin was added into each well and incubated at 37° C. in a humidified $CO_2$ incubator to simulate adhesive degradation. Media samples were collected at 2, 7, and 14 days and these adhesive-conditioned media (ACM) were stored at −20° C. until use. Human dermal fibroblast (HDF) cells were seeded in new 12-well culture plates at a density of $8 \times 10^4$ cells/well and cultured for 24 hours to allow cell attachment. The media was replaced with the stored ACM and cultured for 2 days at 37° C. to evaluate the in vitro cytotoxicity of the various CA derivatives. Cell cytotoxicity by the degraded CA adhesives in ACM was evaluated by MTT assay. The principle of this assay is the addition of a dye which is degraded by enzymes present in living cells, resulting in the formation of a colored product. The product concentration, which is generally directly proportional to the number of viable cells, is assayed by spectrophotometry. FIG. 9 shows the % cell viability after culture with ACM generated in the presence of various CA formulations. ACM from all CA derivatives was not cytotoxic except for the ACM from OCA in the 2 days case. In 7 and 14 days, ACM from CA derivatives without PEG showed no cytotoxicity and ACM from CA derivatives with PEG showed cytotoxicity in order of MCA>OCA+ MCA>OCA.

5. PEG Incorporation Reduces Cell Adhesion to Polymerized Cyanoacrylates

2 μl aliquots of various cyanoacrylate formulations with and without PEG were applied to thin collagen films in 24 well plates and allowed to cure overnight at room temperature. Human dermal fibroblasts were seeded on the collagen film/polymerized adhesive surfaces at $8 \times 10^4$ cells/well and cultured for 48 hours. The cells were stained with fluorescein diacetate and propidium iodide to visualize live (green) and dead (red) cells respectively. FIGS. 10A (OCA+MCA), 10B (OCA+MCA/PEG), 10E (MCA), and 10F (MCA/PEG)

are phase contrast images (black and white) showing the interface between the cyanoacrylate adhesives and the surrounding collagen films and corresponding fluorescent images FIGS. 10C (OCA+MCA), 10D (OCA+MCA/PEG), 10G (MCA), and 10H (MCA/PEG) showing the location of adherent cells. Fibroblasts readily adhered in large numbers to both MCA and OCA+MCA adhesive formulations and the surrounding collagen film. In contrast, the incorporation of PEG into MCA and OCA+MCA adhesives dramatically reduced adhesion to the polymerized adhesive surface. These results suggest that incorporation of PEG reduces the adhesivity of the polymerized adhesive and can reduce the occurrence of undesired tissue adhesions formed between the adhesive and surrounding tissue when applied for internal closure applications.

Example 2

Preparation of Drug-Loaded Poly(butylcyanoacrylate) (PBCA) Particles
A. Polymyxin B-Loaded PBCA Nanoparticles Polymyxin B-loaded polybutylcyanoacrylate (PBCA) particles were prepared by an anionic polymerization method (FIG. 11). Various amounts of polymyxin B were dissolved in various acidic polymerization medium containing different non-ionic surfactants and then various amount of butylcyanoacrylate were slowly added into the polymyxin B-containing polymerization medium under vigorous stirring. The polymerization of the monomer was allowed for four hours at room temperature under vigorous stirring to complete polymerization. When the polymerization was completed, the milky suspension was neutralized by 1N NaOH and then freeze-dried in a lyophilizer. The dried nanoparticles were resuspended in 10 ml distilled water and centrifuged at 15,000 rpm (Beckman centrifuge, JA 17 rotor, Beckman, USA) for an hour at 4° C. and the process was repeated two times to completely remove free drugs and surfactant. The nanoparticles were suspended in water, freeze-dried, and kept in a vacuum desiccator.
B. 5-Fluorouracil-Loaded PBCA Nanoparticles 5-FU-loaded PBCA particles were prepared by anionic polymerization. 100 mg of 5-Fluorouracil (5-FU) was dissolved into 10 ml polymerization medium containing citric acid (0.2 w/v %) and dextran 60-90 kDa (0.8 w/v %) and then 200 mg butylcyanoacrylate monomer was slowly added into 5-FU containing polymerization medium under vigorous stirring. Polymerization of the monomer was allowed for four hours at room temperature under vigorous stirring to complete polymerization. Particles were purified by washing, centrifugation and freeze-dried as described above.
Determination of Drug-Loading Efficiency
A. Polymyxin B The amount of polymyxin B-loaded in the PBCA particles was determined by an HPLC method. HPLC was performed using a reverse phase CI8 column (Regis 10 cm×4.6 mm, 3 um) and employing a binary gradient formed from 0.1% TFA in 75% acetonitrile in water (solution A) and 0.1% TFA in water (solution B) with the following binary gradient: at t=0 min, B=0%, at t=20 min, B=25%, at t=27, B=85%, and at t=30 min, B=85% at flow rate of 0.5 ml/min. The mobile phase was monitored by measuring UV absorbance at 220 nm. Quantitation of polymyxin B was done using a calibration curve constructed from the peak area versus the concentration of standard solution of polymyxin B. The polymyxin B loading efficiency in PBCA nanoparticles was determined as follows:

$$\% \text{ loading} = (D_{t=0} - D_{t=4})/D_{t=0} \times 100 \tag{2}$$

wherein $D_{t=0}$: drug concentration at time 0, and $D_{t=4}$: drug concentration after polymerization at 4 hours. Table V below shows the characteristics of polymyxin B-loaded PBCA nanoparticles prepared by various polymerization conditions.

TABLE V

Preparation of various polymyxin B-loaded nanoparticles

| Amount of Drug (mg) | Amount of BCA (μl) | Anionic Polymerization Medium (10 ml) | Aggregation | Amount of nanoparticle (mg) | Drug loading (%) | Miscibility with OCA monomer |
|---|---|---|---|---|---|---|
| 100 | 100 | 1 w/v % Pluronic F68 (pH 1.5) | no | 94.3 | 23.23 | Not miscible, polymerization |
| 100 | 100 | 1 w/v % Pluronic P105 (pH 1.5) | no | 54.3 | 15.19 | Miscible, no polymerization |
|  | 200 | 1 w/v % Pluronic P105 (pH 1.5) |  | 137.3 | 17.24 |  |
|  |  |  |  | 84.7 | 47.87 |  |
|  |  |  |  | 125.1 | 28.79 |  |
| 100 | 100 | 0.5 w/v % Pluronic F68 and P105 (pH1.5) | no | 69.3 | 23.65 | Miscible no polymerization |
| 100 | 200 |  | no | 88.3 | 20.43 |  |
|  |  |  |  | 153.6 | 19.26 |  |
| 50 | 100 |  | no | 18.3 | 8.79 |  |
| 50 | 200 |  | no | 14.6 | 17.49 |  |

*Miscibility of nanoparticles with OCA monomer was determined by mixing 10 mg of nanoparticles with 100 μl of OCA monomer.

B. 5-Fluorouracil

The amount of 5-FU incorporated in nanoparticles was determined by UV/VIS spectrophotometer. After completion of polymerization, the milky suspension was filtered by 0.2 um membrane filter and the drug concentration in filtrate was calculated using a standard curve constructed from the UV absorbance at 266 nm versus the concentration of standard solution of 5-FU. The 5-FU loading efficiency in PBCA nanoparticles was determined by the same equation (2) as above. Drug-loaded PBCA nanoparticles were analyzed by $^1$H-NMR using DMSO-d6 to determine the structure of drug and polymer in nanoparticles (FIG. 12). Table VI below shows the characteristics of 5-FU-loaded PBCA nanoparticles prepared in various polymerization conditions.

TABLE VI

| Amount of Drug (mg) | Amount of BCA (Hi) | Anionic Polymerization Medium (10 ml) | Aggregation | Amount of nanoparticle | Drug loading (%) | Miscibility with OCA monomer |
|---|---|---|---|---|---|---|
| 100 | 200 | 0.2% Citric acid (pH 2.5) | yes | | | |
| | | 0.2% Citric acid (pH 2.5) and 0.8% Dextran 60-90 kDa | no | 134 mg | 14.55% 14.22% | Miscible, no polymerization |

*Miscibility of nanoparticles with OCA monomer was determined by mixing 10 mg of nanoparticles with 100 µl of OCA monomer.

Evaluation of Antibacterial Activity of Polymyxin B-Loaded PBCA Nanoparticles

Antibacterial activity of polymyxin B-loaded PBCA nanoparticles was measured indirectly by the agar diffusion method. 30 ml of nutrient agar was added into each of four culture plates (90 mm diameter, 15 mm high). After solidifying, a cylindrical hole (13 mm in diameter) was made in the center of the plate and the contents were removed. 10 mg of polymyxin B, PBCA nanoparticles, and two polymyxin B-loaded PBCA nanoparticles (Poly BIPBCA-1 and 2) were added into a hole of each plate, respectively and a few drops of molten agar were added to fix the samples. The plate were inoculated with Escherichia coli and incubated at 37° C. for 24 hours and the zone of inhibition was determined (FIGS. 13A-13D). Polymyxin B-loaded PBCA particles showed similar antibacterial activity (FIGS. 13C and 13D) with free polymyxin B (FIG. 13A), whereas drug-unloaded PBCA particles showed no antibacterial activity (FIG. 13B).

To evaluate the duration of antibacterial activity of each sample, the content of each hole was removed after 24 hours of incubation and transferred to a hole of a freshly prepared plate, incubated again for 24 hours and the zone of inhibition measured. This procedure was continuously repeated until the inhibition of growth was no longer observed. The size of inhibition zone decreased on each successive test period as shown in Table VII below. Polymyxin B loaded-PBCA-1 and -2 (equivalent to 1.93 mg and 1.24 mg of free polymyxin B, respectively) particles showed same duration of antibacterial activity with free polymyxin B although the amount of polymyxin B in the nanoparticles used was less than about 5 and 8 times of the free polymyxin B.

TABLE VII

Antibacterial activity of polymyxin B-loaded PBCA particles using *Escherichia coli*

| | Inhibition zone in days: Diameter (mm)$^a$ Sample$^b$ | | | | | |
|---|---|---|---|---|---|---|
| | 1 | 2 | 3 | 4 | 5 | 6 |
| Polymyxin B | 36 | 38.3 | 28 | 25.1 | 22 | c |
| PBCA | c | | | | | |
| PolyB/PBCA-1 | 28 | 25.1 | 21.5 | 18.5 | 17.5 | c |
| Poly B/PBCA-2 | 30 | 23.5 | 23.5 | 16 | 15.4 | c |

$^a$Data include the original size of the sample (13 mm in diameter).
$^b$10 mg of free polymyxin B and 10 mg of PBCA, PolyB/PBCA-1 and 2 equivalent to 1.93 mg and 1.24 mg of free Poly B) were used for the test
c Inhibition of growth not observed.

Discussion of Results

Example 1 evaluated the efficacy of cyanoacrylate adhesive formulations incorporating PEG. Longer alkyl side chains showed longer degradation rates as compared to shorter alkyl side chains. Also, the presence of PEG increased degradation rates in all cyanoacrylate formulations, and also increased the bond strength with skin. In vivo biocompatibility studies showed that longer alkyl side chains showed the least degradation and thicker cell layers, and addition of PEG increased degradation. Cell cytotoxicity was evaluated, and PEG was found to reduce undesirable cell adhesion to the adhesive surface.

Example 2 showed that drug particles can be successfully loaded into PCBA nanoparticles and released from the nanoparticles. Using the findings from Example 1 in conjunction with the findings of Example 2, cyanoacrylate adhesive formulations can be made including PCBA drug-containing nanoparticles to have the degradation rate, bond strength, and cell adhesion desired.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The invention claimed is:

1. A composition, comprising:
 a tissue adhesive having:
  a cyanoacrylate monomer selected from the group consisting of methoxyisopropylcyanoacrylate, octylcyanoacrylate, and methoxyisopropylcyanoacrylate; and
  polyethylene glycol (PEG) that remains a polyether in the adhesive, and
 polymerized cyanoacrylate nanoparticles containing an effective amount of a therapeutic agent,
 wherein said nanoparticles are homogenously mixed together and miscible with the adhesive, and, when mixed together with the adhesive, remain miscible in the adhesive and do not initiate polymerization of the cyanoacrylate monomer.

2. The tissue adhesive composition of claim 1, wherein said therapeutic agent is selected from the group consisting of antibacterial agents, antifungal agents, anticancer agents, and anti-inflammatory drugs.

3. The tissue adhesive composition of claim 2, wherein said therapeutic agent is an antibacterial agent selected from the group consisting of polymyxin B sulfate, neomycin sulfate, gentamycin sulfate, gramicidin, zinc bacitracin, and hydroxyquinolone.

4. The tissue adhesive composition of claim 2, wherein said therapeutic agent is an antifungal agent selected from the group consisting of terbinafine, clotrimazole, ketokonazole, nystatin, and amphotericin B.

5. The tissue adhesive composition of claim 2, wherein said therapeutic agent is an anticancer agent selected from the group consisting of 5-fluorouracil, doxorubicin, and paclitaxel.

6. The tissue adhesive composition of claim 2, wherein said therapeutic agent is an anti-inflammatory agent selected from the group consisting of ibuprofen, ketoprofen, dexamethasone, and predisolone.

7. The tissue adhesive composition of claim 1, wherein said composition is formulated in a patch.

8. The tissue adhesive composition of claim 7, wherein said composition is formulated in a patch and said therapeutic agent is chosen from the group consisting of nicotine and glucose.

9. The tissue adhesive composition of claim 1, wherein the tissue adhesive composition is bioabsorbed within 12 weeks when applied to an internal tissue of a wound or incision.

* * * * *